United States Patent

Sui et al.

(10) Patent No.: US 6,821,993 B1
(45) Date of Patent: Nov. 23, 2004

(54) TRIAZEPINE DERIVATIVES AS NEUROTROPHIC AGENTS

(75) Inventors: Zhihua Sui, Flemington, NJ (US); Shawn P. Walsh, Branchburg, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/264,407

(22) Filed: Oct. 4, 2002

Related U.S. Application Data

(60) Provisional application No. 60/326,927, filed on Oct. 4, 2001.

(51) Int. Cl.[7] .................. C07D 487/04; C07D 513/04; A61K 31/55; A61P 25/16; A61P 25/28

(52) U.S. Cl. ...................... 514/338; 514/368; 514/413; 540/492; 540/501

(58) Field of Search ................................ 514/338, 368, 514/413; 540/492, 501

(56) References Cited

U.S. PATENT DOCUMENTS 3,635,983 A    1/1972    Ratouis et al.

FOREIGN PATENT DOCUMENTS

WO    WO 97/22619 A    6/1997

OTHER PUBLICATIONS

M.A. Mahran et al., "Synthesis of Some Novel Perhydrotriazepine–3, 6–diones of Potential Antifungal Activity", Alex. J. Pharm. Sci., vol. 10, No. 2, Jun. 1996, XP001097508.

Primary Examiner—Bruck Kifle

(57) ABSTRACT

This invention relates to a series of triazepines of Formula I and II,

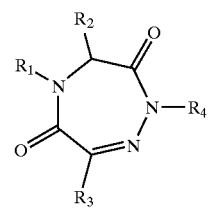

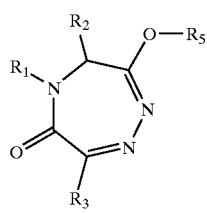

and pharmaceutical compositions containing them. The compounds of the invention have neurotrophic activity and are useful in the treatment and prevention of neuronal disorders such as Parkinson's disease, Alzheimer's disease, stroke, multiple sclerosis, amyotrophic lateral sclerosis diabetic neuropathy and Bell's palsy.

12 Claims, No Drawings

TRIAZEPINE DERIVATIVES AS NEUROTROPHIC AGENTS

This invention claims priority from U.S. Provisional Application No. 60/326,927 filed Oct. 4, 2001 and entitled "Triazepine Derivatives as Neurotrophic Agents," the contents of which is incorporated herein by reference in its entirety.

FIELD OF THE INVENTION

This invention relates to certain novel triazepines having neurotrophic activity. These compounds, along with related compositions and methods, are useful in the treatment and prevention of neuronal disorders such as Parkinson's disease, Alzheimer's disease, stroke, multiple sclerosis, amyotrophic lateral sclerosis, diabetic neuropathy, and Bell's palsy.

BACKGROUND OF THE INVENTION

Neurodegenerative diseases constitute a major threat to public health throughout the world. One of the most serious of such diseases is Alzheimer's disease (AD), a major cause of dementia in aged humans and the fourth most common medical cause of death in the United States. In the U.S., it is estimated that AD afflicts two to three million individuals overall, and more than 5% of the population over the age of 65. Although the exact etiology of AD remains to be defined, the disease is characterized by the presence of a large number of amyloid plaques and neurofibrillary tangles in regions of the brain involved in cognitive function, and degeneration of cholinergic neurons that ascend from the basal forebrain to cortical and hippocampal areas. Currently, there are no effective therapies for AD (Brinton, R. D. and Yamazaki, R. S., *Pharm. Res.*, 1998, 15:386–98).

Similar to AD, Parkinson's Disease (PD) is a progressive degenerative disease of the central nervous system (CNS). The lifetime incidence of the disease is approximately 2% in the general population. In PD, degeneration of the dopaminergic neurons of the substantia nigra leads to a decrease in dopamine levels in the region of the brain controlling voluntary movement, the corpus striatum. Therefore, standard treatments have focused on the administration of agents, like L-dopa and bromocriptine, which replenish dopamine levels in the affected areas of the brain. Dopaminergic regimens lose their efficacy, however, as nerve cells continue to die and the disease progresses. At the same time the involuntary tremors seen in the early stages of PD advance to periods of difficult movement and, ultimately, to immobility. Therefore, alternative therapies are actively being sought (Pahwa, R. and Koller, W. C., *Drugs Today*, 1998, 34:95–105).

Neurodegenerative diseases of the somatosensory nervous system also constitute a class of debilitating and potentially lethal conditions. Amyotrophic lateral sclerosis (ALS) is a fatal disease characterized by progressive degeneration of the upper and lower motor neurons. Although the precise etiology of ALS is unknown, popular theories suggest that excitotoxicity and/or oxidative stress are contributing factors. Riluzole is the first drug approved and marketed for ALS. It possesses antiexcitotoxic properties and has been shown to increase the rate of survival of ALS patients. However, the drug is not a cure, and clinical trials of alternative agents are currently underway (Louvel, E., Hugon, J. and Doble, A., *Trends Pharmacol. Sci.*, 1997, 18:196–203).

Peripheral neuropathies are secondary to a number of metabolic and vascular conditions. In particular, approximately 30% of patients with diabetes mellitus suffer from some form of peripheral neuropathy that may affect either the small myelinated fibers, causing loss of pain and temperature sensation, or the large fibers, causing motor or somatosensory defects. Pharmacotherapeutic intervention tends to be symptomatic, and the best approach to treatment and prevention remains the maintenance of normal blood glucose levels through diet and insulin administration (Biessels, G. J. and Van Dam, P. S., *Neurosci. Res. Commun.*, 1997, 20:1–10).

A considerable body of evidence now suggests that deficiencies in the levels of certain proteinaceous growth factors, or neurotrophic factors, may play key pathoetiological roles in both peripheral and central neurodegenerative diseases (Tomlinson et al., Diabetes, 1997, 46(suppl. 2):S43–S-49; Hamilton, G. S., *Chem. Ind.*, (London) 1998, 4:127–132; Louvel et al., *Trends Pharmacol. Sci.*, 1997, 18:196–203; Ebadi et al., *Neurochem. Int.*, 1997, 30:347–374).

These neurotrophic factors can be divided into two structural classes: 1) the neurotrophins, including nerve growth factor (NGF); glial cell-derived neurotrophic growth factor (GDNF); brain-derived neurotrophic factor (BDNF); neurotrophin 3 (NT-3); neurotrophin 4/5 (NT-4/5); neurotrophin 2 (NT-2); and ciliary neurotrophic factor (CNTF) which is related to the cytokine family of molecules. All neurotrophic factors promote neurite outgrowth, induce differentiation, and suppress programmed cell death or apoptosis in specific subpopulations of peripheral and central neurons. For example, NGF exerts trophic effects on sympathetic and sensory neurons of the dorsal root ganglion and cholinergic neurons of medial septum in the CNS, suggesting potential therapeutic utility in AD. CNTF has trophic actions on a broad cross-section of neurons, including parasympathetic, sensory, sympathetic, motor, cerebellar, hippocampal, and septal neurons. Of particular interest is the fact that CNTF partially prevents the atrophy of skeletal muscle following the formation of nerve lesions but has no effect on innervated muscle, indicating that CNTF is primarily operative in the pathological state. As a result, CNTF is currently being evaluated for its effects in musculoskeletal diseases like ALS.

The clinical utility of proteinaceous neurotrophic agents is severely hampered by their limited bioavailability, especially in the CNS. This necessitates the administration of these agents directly into the brain to induce a therapeutic effect. Administration to the brain can be a relatively hazardous and a cumbersome route of administration.

Protein based compounds currently in clinical use as neurotrophic agents cannot be administered orally and otherwise show poor bioavailability except when administered intracerebroventricularly (ICV) for a CNS indication or intravenously for peripheral nerve dysfunctions such as diabetic neuropathy or Bell's palsy. Accordingly, there is a clear need for bioavailable small molecule mimetics of neurotrophic factors that are orally bioavailable and can readily penetrate the blood-brain barrier.

Great efforts have been made to identify small molecules having neurotrophic activity, but all such compounds reported so far are structurally dissimilar to triazepines.

SUMMARY OF THE INVENTION

This invention provides novel triazepine compounds having surprising neurotrophic activity. Demonstrated to have these biological activities by in vitro and in vivo assays described hereinafter are the compounds of the present invention as shown in Formula I and II:

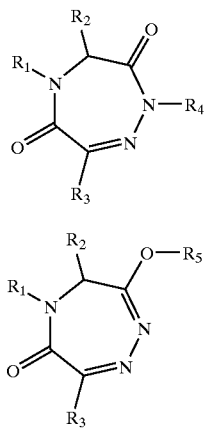

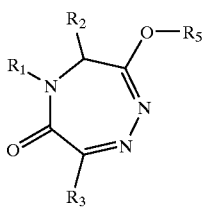

or a pharmaceutically acceptable salt thereof, wherein $R_1$, $R_2$, $R_3$, and $R_4$ are independently selected from hydrogen, $C_1$–$C_{10}$ alkyl, aryl, and heterocyclyl, or $R_1$, the nitrogen atom attached to $R_1$, and $R_2$ together form a 4- to 8-membered heterocycle having 1 to 4 heteroatoms selected from the group consisting of S, O, and N; and $R_5$ is selected from $C_1$–$C_{10}$ alkyl, aryl, and heterocyclyl, or $R_1$, the nitrogen atom attached to $R_1$, and $R_2$ together form a 4- to 8-membered heterocycle having 1 to 4 heteroatoms selected from the group consisting of S, O, and N.

This invention also provides a pharmaceutical composition comprising the instant compound and a pharmaceutically acceptable carrier, as well as related synthetic methods.

This invention further provides a method of treating a subject suffering from a condition characterized by neuronal damage caused by disease or trauma, which method comprises administering to the subject a therapeutically effective dose of the instant pharmaceutical composition.

This invention still further provides a method of inhibiting in a subject the onset of a condition characterized by neuronal damage caused by disease or trauma, which method comprises administering to the subject a therapeutically effective dose of the instant pharmaceutical composition.

DETAILED DESCRIPTION OF THE INVENTION

This invention provides novel triazepine compounds having surprising neurotrophic activity. These compounds, along with related pharmaceutical compositions and methods, are useful in the treatment and prevention of neuronal disorders including, for example, Parkinson's disease, Alzheimer's disease, stroke, multiple sclerosis, amyotrophic lateral sclerosis, diabetic neuropathy or Bell's palsy. They are also useful in the treatment of disorders caused by trauma to the brain, spinal cord or peripheral nerves.

Specifically, this invention provides a compound of Formula I or II,

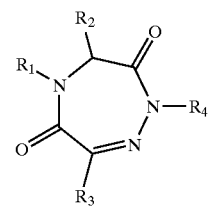

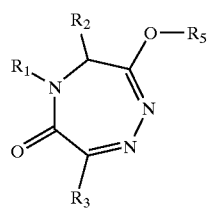

or a pharmaceutically acceptable salt thereof, wherein $R_1$, $R_2$, $R_3$, and $R_4$ are independently selected from hydrogen, $C_1$–$C_{10}$ alkyl, aryl, and heterocyclyl, or $R_1$, the nitrogen atom attached to $R_1$, and $R_2$ together form a 4- to 8-membered heterocycle having 1 to 4 heteroatoms selected from the group consisting of S, O, and N; and $R_5$ is selected from $C_1$–$C_{10}$ alkyl, aryl, and heterocyclyl, or $R_1$, the nitrogen atom attached to $R_1$, and $R_2$ together form a 4- to 8-membered heterocycle having 1 to 4 heteroatoms selected from the group consisting of S, O, and N.

More specifically, this invention provides a compound of Formula Ia or IIa,

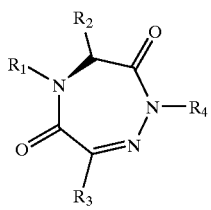

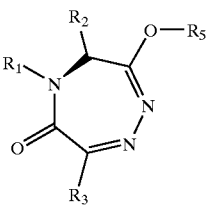

wherein $R_1$, $R_2$, $R_3$, $R_4$, and $R_5$ are as described above.

In one embodiment of the instant compound, $R_4$ is hydrogen or a $C_1$–$C_{10}$ alkyl substituted with an aryl or an N-containing heterocyclyl. In another embodiment, $R_3$ is a $C_4$–$C_{10}$ alkyl. In yet another embodiment, $R_1$, the nitrogen atom attached to $R_1$, and $R_2$ together form a 4- to 8-membered heterocycle having 1 to 4 heteroatoms selected from the group consisting of S, O, and N. More particularly, $R_1$, the nitrogen atom attached to $R_1$, and $R_2$ together form

Unless specified otherwise, the term "alkyl" refers to a straight, branched or cyclic substituent consisting solely of carbon and H with or without unsaturation, optionally substituted with one or more independent groups including, but not limited to, halogen (F, Cl, Br, I), OH, amino, alkoxy, aryl, substituted aryl, heteroaryl, substituted heteroaryl, heterocyclyl, and substituted heterocyclyl. The term "alkoxy" refers to O-alkyl where alkyl is as defined supra. The term "halo" or "halogen" means fluoro, chloro, bromo or iodo.

The term "aryl" or "aromatic ring" refers to a 5- to 6-membered ring containing a 6-electron delocalized conjugated pi bonding system such as phenyl, furanyl, and pyrrolyl. The term "aryl" or "aromatic ring" includes mono and fused aromatic rings such as phenyl, naphthyl, diphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. The symbol "Ph" refers to phenyl.

The term "heteroaryl" as used herein represents a stable five or six-membered monocyclic or bicyclic aromatic ring system which consists of carbon atoms and from one to three heteroatoms selected from N, O and S. The heteroaryl group may be attached at any heteroatom or carbon atom, which results in the creation of a stable structure. Examples of heteroaryl groups include, but are not limited to pyridinyl, pyrazinyl, pyridazinyl, pyrimidinyl, thiophenyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl or quinolinyl.

Unless specified otherwise, aryl or heteroaryl may be substituted by one to three independent groups such as halogen, aryl, heteroaryl, OH, CN, mercapto, nitro, $C_{1-10}$-alkyl, halo-$C_{1-10}$-alkyl, $C_{1-10}$-alkoxy, $C_{1-10}$-alkylthio, amino, $C_{1-10}$-alkyl-amino, di($C_1$–$C_8$-alkyl-)amino, arylamino, nitro, formyl, carboxyl, alkoxycarbonyl, $C_{1-10}$-alkyl-CO—O—, $C_{1-10}$-alkyl-CO—NH—, and carboxamide. Substituted-heteroaryl may also be substituted with a substituted-aryl or a second substituted-heteroaryl to give, for example, a 2-phenylpyrimidine or a 2-(pyrid-4-yl)pyrimidine, and the like.

"Heterocyclyl" or "heterocycle" is a 3- to 8-member saturated or partially saturated, single or fused ring system which consists of carbon atoms and from one to four heteroatoms selected from N, O and S. Unless specified otherwise, the heterocyclyl group may be attached at any heteroatom or carbon atom which results in the creation of a stable structure. Examples of heterocyclyl groups include, but are not limited to pyridine, pyrimidine, oxazoline, pyrrole, imidazole, morpholine, furan, indole, benzofuran, pyrazole, pyrrolidine, piperidine, and benzimidazole. "Heterocyclyl" or "heterocycle" may be substituted with one or more independent groups including, but not limited to, H, halogen, oxo, OH, $C_1$–$C_{10}$ alkyl, amino, and alkoxy.

The instant compounds can be isolated and used as free bases. They can also be isolated and used as pharmaceutically acceptable salts. The phrase "pharmaceutically acceptable salt" denotes salts of the free base which possess the desired pharmacological activity of the free base and which are neither biologically nor otherwise undesirable. These salts may be derived from inorganic or organic acids. Examples of inorganic acids are hydrochloric acid, hydrobromic acid, hydroiodic acid, perchloric acid, nitric acid, sulfuric acid and phosphoric acid. Examples of organic acids are acetic acid, propionic acid, glycolic acid, lactic acid, pyruvic acid, malonic acid, succinic add, malic acid, maleic acid, maleic acid, fumaric acid, tartaric acid, citric acid, benzoic acid, cinnamic acid, mandelic acid, oxalic acid, pamoic acid, saccharic acid, methanesulfonic acid, ethanesulfonic acid, p-toluenesulfonic acid, methyl sulfonic acid, salicyclic acid, hydroethanesulfonic acid, benzenesulfonic acid, 2-naphthalenesulfonic acid, p-toluenesulfonic acid, cyclohexanesulfamic acid and the like. Alternatively, "pharmaceutically acceptable salt" denotes salts of the free acid which possess the desired pharmacological activity of the free acid and which are neither biologically nor otherwise undesirable. These salts may be derived from a metal ion or an organic base, such as Li, Na, K, $NH_4$ and the like.

Where the compounds according to this invention have one or more stereogenic centers, it is to be understood that all possible optical isomers, antipodes, enantiomers, and diastereomers resulting from additional stereogenic centers that may exist in optical antipodes, racemates and racemic mixtures thereof are also part of this invention. The antipodes can be separated by methods known to those skilled in the art such as, for example, fractional recrystallization of diastereomeric salts of enantiomerically pure acids. Alternatively, the antipodes can be separated by chromatography in a Pirkle-type column.

Some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The following compounds are exemplary of the present invention:

1H-pyrrolo[2,1-d][1,2,5]triazepine-1,5(2H)-dione, 4-(1,1-dimethylpropyl)-7,8,9,9a-tetrahydro-;

1H-pyrrolo[2,1-d][1,2,5]triazepine-1,5(2H)-dione, 4-(1,1-dimethylpropyl)-7,8,9,9a-tetrahydro-, (9aS)-;

1H-pyrrolo[2,1-d][1,2,5]triazepine-1,5(2H-dione, 4-(1,1-dimethylpropyl)-7,8,9,9a-tetrahydro-2-[3-(3-pyridinyl)propyl]-, (9aS)-;

1H-pyrrolo[2,1-d][1,2,5]triazepine-1,5(2H)-dione, 4-(1,1-dimethylpropyl)-7,8,9,9a-tetrahydro-2-(3-phenylpropyl)-, (9aS)-;

1H,7H-thiazolo[4,3-d][1,2,5]triazepine-1,5(2H)-dione, 9,9a-dihydro-4-(2-thienyl)-, (9aR)-; and 1H, 7H-thiazolo[4,3-d][1,2,5]triazepine-1,5(2H)-dione, 2-(3,3-diphenylpropyl)-9,9a-dihydro-4-(2-thienyl)-, (9aR)-.

This invention also provides a pharmaceutical composition comprising the instant compound and a pharmaceutically acceptable carrier.

Pharmaceutical compositions containing the compound of the present invention as the active ingredient in intimate admixture with a pharmaceutical carrier can be prepared according to conventional pharmaceutical techniques. The carrier may take a wide variety of forms depending on the form of preparation desired for administration, such as topical administration and systemic administration including, but not limited to, intravenous infusion, oral, nasal or parenteral. In preparing the compositions in oral dosage form, any of the usual pharmaceutical carriers may be employed, such as water, glycerol, glycols, oils, alcohols, flavoring agents, preservatives, coloring agents, syrup and the like in the case of oral liquid preparations (for example, suspensions, elixirs and solutions); or carriers such as starches, sugars, methyl cellulose, magnesium sterate, dicalcium phosphate, mannitol and the like in the case of oral solid preparations (for example, powders, capsules and tablets). All excipients may be mixed as needed with disintegrants, diluents, granulating agents, lubricants, binders and the like using conventional techniques known to those skilled in the art of preparing dosage forms.

The preferred route of administration is oral administration. Because of their ease in administration, tablets and capsules represent an advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

This invention also provides a method of stimulating neuronal growth comprising contacting neurons with an effective amount of the instant compound. The contacting can be performed, for example, in vitro, ex vivo or in vivo.

The compounds of the present invention stimulate neuronal growth. Thus, this invention further provides a method of treating a subject suffering from a condition characterized by neuronal damage caused by disease or trauma, which method comprises administering to the subject a therapeutically effective dose of the instant pharmaceutical composition. As used herein, the term subject" includes, without limitation, any animal or artificially modified animal. In the preferred embodiment, the subject is a human.

In one embodiment, the disorder treated is caused by a disease selected from the group consisting of Parkinson's disease, Alzheimer's disease, stroke, multiple sclerosis, amyotrophic lateral sclerosis, peripheral neuropathy and Bell's palsy. In another embodiment, the disorder treated is caused by trauma to the brain, spinal cord or peripheral nerves. In a preferred embodiment, the condition is Alzheimer's disease.

This invention still further provides a method of inhibiting in a subject the onset of a condition characterized by neuronal damage caused by disease or trauma, which method comprises administering to the subject a prophylactically effective dose of the instant pharmaceutical composition. In a preferred embodiment, the condition is Alzheimer's disease.

As used herein, "treating" a disorder means eliminating or otherwise ameliorating the cause and/or effects thereof. "Inhibiting" the onset of a disorder means preventing, delaying, or reducing the physical manifestations of the disease, or reducing the likelihood of such onset. Likewise, "therapeutically effective" and "prophylactically effective" doses are doses that permit the treatment and inhibition, respectively, of a disorder. Methods are known in the art for determining therapeutically and prophylactically effective doses for the instant pharmaceutical composition. The effective dose for administering the pharmaceutical composition to a human, for example, can be determined mathematically from the results of animal studies.

In one embodiment, oral doses of the instant compounds range from about 0.01 to about 200 mg/kg, daily. In another embodiment, oral doses range from about 0.1 to about 50 mg/kg daily, and in a further embodiment, from about 1 to about 30 mg/kg daily. Infusion doses can range, for example, from about 1.0 to $1.0 \times 10^4$ μg/kg/min of instant compound, admixed with a pharmaceutical carrier over a period ranging from several minutes to several days. For topical administration, the instant compound can be mixed with a pharmaceutical carrier at a concentration of, for example, about 0.1 to about 10% of drug to vehicle.

Finally, this invention provides processes for preparing the instant compounds. These compounds can be prepared as shown below from readily available starting materials and/or intermediates following processes well known in the art.

This invention will be better understood by reference to the Experimental Details that follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

Experimental Details

A. Schemes and Syntheses

The synthesis of the claimed compounds is summarized in Schemes I, II, and III wherein $R_1$, $R_2$, $R_3$, $R_4$, and $R_5$ are as described hereinabove, $R_{3a}$ is $R_3$ other than H, X is preferably halogen or OH, and $R_A$ and $R_B$ are optionally substituted alkyl (preferably lower alkyl or benzyl).

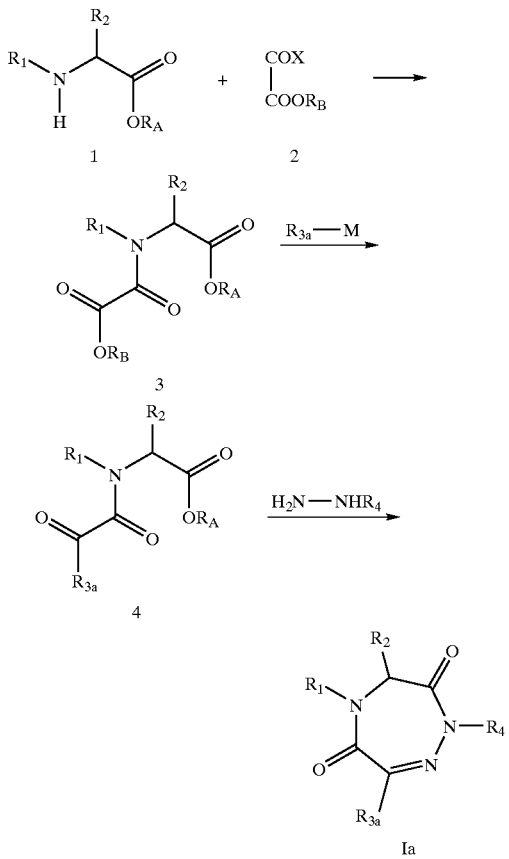

Scheme I

Amino acid derivatives 1 can be reacted with oxalic acid derivatives 2 to give compounds of formula 3. When X is a halogen such as chloro or bromo, the reaction can be carried out in an organic solvent, preferably THF (tetrahydrofuran), DCM (dichloromethane), ether, or dioxane, at a temperature preferably between −78° C. and 80° C. in the presence of an organic or inorganic base, preferably TEA (triethylamine), DIEA (diisopropylethylamine), or NaHCO$_3$. When X is OH, the reaction can be carried out in an organic solvent, preferably THF, DMF (N,N-dimethylformamide), or DCM, in the presence of a coupling reagent, preferably DCC (dicyclohexylcarbodiimide) or HOBt (1-hydroxybenzotriazole), at a temperature preferably between 15° C. and 80° C. Compounds of formula 3 can then be converted to compounds of formula 4 with an organometalic reagent R$_3$-M wherein M is preferably Li or MgY (Y=halogen). Compounds of formula 4 can be treated with a hydrazine in the presence of a base, preferably TEA or DIEA, in an organic solvent or a mixture of water with an appropriate organic solvent such as dioxane and ethanol at a temperature preferably between 60–120° C. to give compounds of formula Ia.

Scheme II

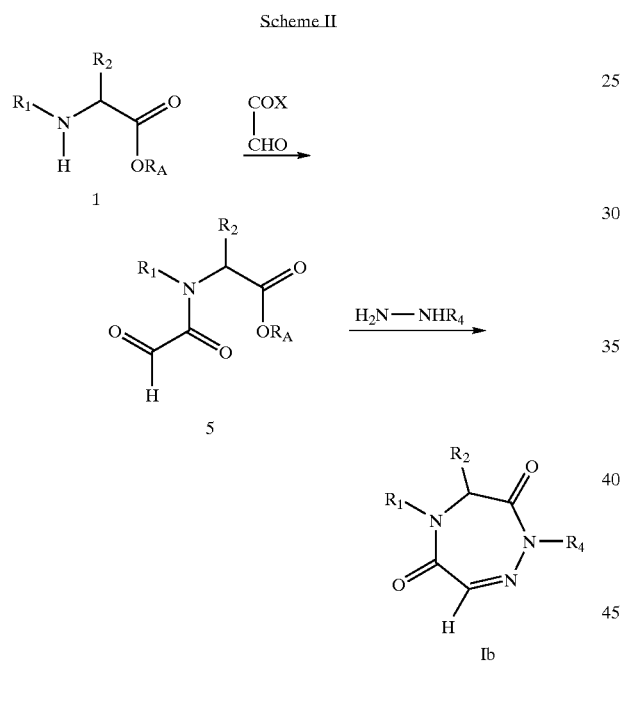

When R$_3$ is a hydrogen as shown in Scheme II, compound 1 is reacted with XCO—CHO under similar conditions as described in Scheme I to give 5. The intermediates 5 can be converted to compounds of formula Ib by reaction with hydrazine.

Scheme III

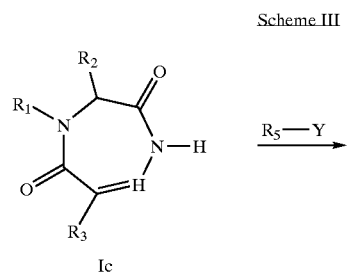

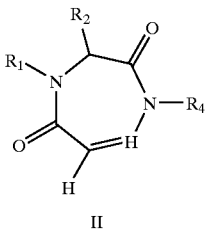

When R$_4$ is a hydrogen as shown in Scheme III, compounds Ic can be further modified by alkylations with various alkylating agents, preferably halides, triflates, or sulfonates, to give compounds of formulae Id and II. Compounds of formula Id and II may be readily separated by know methods such as chromatography.

The examples below describe in greater particularity the chemical synthesis of representative compounds of the present invention. The remaining compounds disclosed herein can be prepared similarly in accordance with one or more of these methods. No attempt has been made to optimize the yields obtained in these reactions, and it would be clear to one skilled in the art that variations in reaction times, temperatures, solvents, and/or reagents could increase such yields.

EXAMPLE 1

Compound (1)

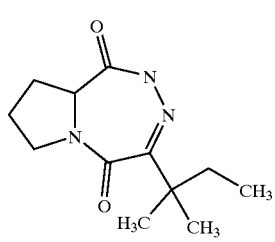

1H-pyrrolo[2,1-d][1,2,5]triazepine-1,5(2H)-dione, 4-(1,1-dimethylpropyl)-7,8,9,9a-tetrahydro-, (9aS)-

Anhydrous hydrazine (0.28 g, 8.58 mmol) was added dropwise to a solution of 2(S)-methyl 1-(1,2-dioxo-3,3-dimethylpentyl)proline (2.0 g, 7.8 mmol) in ethanol (400 ml). The solution was stirred 30 min. at 25° C., then was heated to reflux for 3 hrs, followed by concentration. The residue was dissolved in xylenes (100 ml), and heated to reflux for 8 hrs, followed by concentration. The product was obtained by triturating the residue in ethyl acetate with pentane to yield 5.2 g of product as white solid (28%). $^1$H NMR (d$_6$-DMSO): δ 0.78 (t, 3H); 1.19 (2 overlapping s's, 6H); 1.62 (m, 2H); 1.83 (m, 2H); 1.98 (m, 1H); 2.44 (m, 2H); 3.27 (m, 1H); 3.58 (m, 1H); 4.10 (m, 1H).

EXAMPLE 2

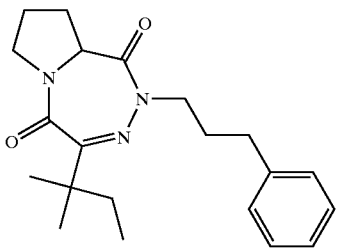

Compound (2)

1H-pyrrolo[2,1-d][1,2,5]triazepine-1,5(2H)-dione, 4-(1,1-dimethylpropyl)-7,8, 9,9a-tetrahydro-2-(3-phenylpropyl)-, (9aS)-

Potassium Hexamethyldisilazane (0.5 M solution in THF, 0.17 mmol) was added to a solution of (1) (0.04 g, 0.17 mmol) in DMF (5 ml) at 0° C. The solution was warmed to 25° C. and stirred for 1 hr, then 1-bromo-3-phenylpropane (0.068 g, 0.34 mmol) was added, and the solution was stirred 20 hrs at 25° C. The solution was diluted with sat. ammonium chloride and extracted to ethyl acetate. The organics were combined and washed with water and brine, then dried (MgSO$_4$), and concentrated. The residue was purified by column chromatography (silica gel, 98:2, dichloromethane:methanol) to yield 0.034 g of product as clear oil (56%). $^1$H NMR (CDCl$_3$): δ 0.86 (t, 3H); 1.27 (2 overlapping s's, 6H); 1.69 (m, 2H); 1.96 (overlaping m's, 5H); 2.49 (t, 2H); 2.73 (m, 1H); 3.36 (m, 1H); 3.74 (m, 2H); 3.89 (m, 2H); 7.17 (m, 3H); 7.28 (m, 2H).

EXAMPLE 3

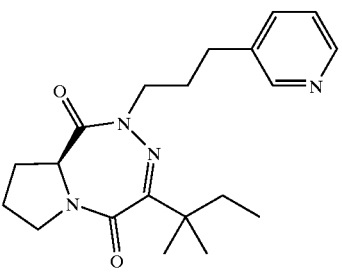

Compound (3)

1H-pyrrolo[2,1-d][1,2,5]triazepine-1.5(2H)-dione, 4-(1,1-dimethylpropyl)-7,8,9,9a-tetrahydro-2-[3-(3-pyridinyl)propyl]-, (9aS)-

Thionyl chloride (2.6 g, 22.2 mmol) was added dropwise to a solution of 3-(3-pyridyl)-1-propanol (2.0 g, 14.6 mmol) in chloroform (10 ml) at 0° C. The solution was warmed to 25° C. and stirred 20 hrs. The solution was poured over ice and extracted to ethyl acetate. The organics were combined, dried (MgSO$_4$), and concentrated, to yield 1.68 g of 1-chloro-3-(3-pyridyl)propane hydrochloride (68%) which was used without further purification. Potassium hexamethyldisilazane (0.5 M solution in THF, 1.92 mmol) was added to a solution of (1) (0.39 g, 1.6 mmol) in DMF (5 ml) at 0° C. with potassium iodide (0.16 mmol) and 18-c-6 (0.16 mmol). This mixture was warmed to 25° C. and stirred 1 hr, after which 1-chloro-3-(3pyridyl)propane was added dropwise, and the reaction stirred 20 hrs. The solution was cooled to 0° C., and neutralized with the dropwise addition of saturated NH$_4$Cl (5 ml). The mixture was warmed to 25° C., diluted with saturated NH$_4$Cl, and extracted with ethyl acetate. The organics were combined, dried (MgSO$_4$), and concentrated. The residue was purified by column chromatography (silica gel, 65:36, pentane:ethyl acetate) to yield 0.073 g of product as clear oil (13%). $^1$H NMR (CDCl$_3$): δ 0.86 (t, 3H); 1.28 (2 overlapping s's, 6H); 1.71 (m, 2H); 1.98 (overlaping m's, 5H); 2.59 (t, 2H); 2.73 (m, 1H); 3.38 (m, 1H); 3.75 (m, 2H); 3.89 (m, 2H); 7.21 (m, 1H); 7.49 (m, 1H); 8.45 (m, 2H).

EXAMPLE 4

2(S) Methyl 1-(1.2-dioxo-2-(2-thiophene)ethane)-4-thioproline

Oxalyl chloride (4.56 g, 35.4 mmol) was added to a solution of 2-thiophene-glyoxilic acid (5.11 g, 32.6 mmol) in dichloromethane (20 ml) at 0° C. After 10 min, DMF (several drops) was added into the solution. The solution was warmed to 25° C. and stirred for 30 min, and then concentrated. The residue was dissolved in dichloromethane (10 ml) and added dropwise to a solution of 2(S)-Methyl 4-thioproline hydrochloride (5.0 g, 27.2 mmol) with triethylamine (3.6 g, 35.4 mmol) in dichloromethane (40 ml). The reaction was stirred for 20 hrs, then was filtered through celite and concentrated. The residue was purified by column chromatography (silica gel, 60:40, pentane:ethyl acetate) to yield 6.65 g of product as brown oil (87%). NMR shows doubling of resonances due to amide bond rotamers. $^1$H NMR (CDCl$_3$): δ 3.38 (m, 2H); 3.67, 3.84 (2 s's, 3H); 4.76 (m, 2H); 5.19, 5.41 (2 m's, 1H); 7.23 (m, 1H); 7.34 (m, 1H); 8.10 (m, 1H).

EXAMPLE 5

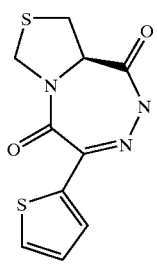

Compound (5)

1H,7H-thiazolo[4,3-d][1,2,5]triazepine-1,5(2H)-dione, 9,9a-dihydro-4-(2-thienyl)-, (9aR)-

Anhydrous hydrazine (0.78 g, 24.5 mmol) was added dropwise to a solution of (4) (6.65 g, 23.3 mmol) in ethanol (600 ml) and the mixture was heated to reflux for 3 hrs. The reaction was cooled and concentrated. The residue was dissolved in chlorobenzene (100 ml), and the solution heated to reflux for 8 hrs. The reaction was allowed to cool and was concentrated. The residue was triturated with ethyl acetate and filtered to provide 1.3 g of product as pale yellow solid (21%). $^1$H NMR (CDCl$_3$): δ 3.27 (overlapping m's, 2H); 3.57 (m, 1H); 4.53 (m, 1H); 4.81 (m, 1H); 7.17 (m, 1H); 7.52 (m, 1H); 7.71 (m, 1H).

EXAMPLE 6

Compound (6)

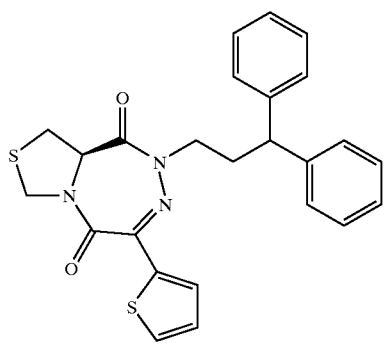

1H,7H-thiazolo[4,3-d][1,2,5]triazepine-1,5(2H)-dione, 2-(3,3-diphenylpropyl)-9,9a-dihydro-4-(2-thienyl)-, (9aR)-

Potassium hexamethyldisilazane (0.5 M solution in THF, 1.13 mmol) was added to a solution of (5) (0.259, 0.94 mmol) in DMF (5 ml) with potassium iodide (0.094 mmol) at 0° C. The solution was warmed to 25° C. and stirred 20 min, followed by the addition of 1-bromo-3,3-diphenylpropane. The solution was stirred 20 hrs, then was diluted with saturated $NH_4Cl$ and extracted to ethyl acetate. The organics were combined and washed with brine, dried ($MgSO_4$), and concentrated. The residue was purified by column chromatography (silica gel, 70:30, pentane:ethyl acetate) to yield 0.12 g of product as clear oil (28%). $^1$H NMR ($CDCl_3$). δ 2.53 (overlapping m's, 2H); 3.21 (m, 1H); 3.82 (m, 2H); 4.05 (overlapping m's, 3H); 4.68 (m, 2H); 7.14 (m, 3H); 7.29 (m, 7H); 7.50 (m, 1H); 7.77 (m, 1H).

B. Assays

Results from Examples 7, 8, and 9 are shown in Table 1. Examples 8 and 9 detail the methods used for preparation of the cell cultures used in Example 10.

EXAMPLE 7

Dorsal Root Ganglion (DRG) Culture

DRG were dissected from newborn or 1-day-old CD rats and placed into PBS on ice. After rinsing twice with sterile plating medium, DRG were transferred to empty wells of a 6-well plate coated with polyornithine/laminin (Becton Dickinson Labware) using #7 curved forceps. Three ml/well of plating medium were then added very gently, so as not to disturb the DRG plating medium is Leibovitz's L-15 medium (Gibco), plus 0.6% glucose, 33 mM KCl, 10% FCS, 10 mM Hepes and penicillin/streptomycin/glutamine. After overnight incubation at about 37° C. in 5% $CO_2$, this medium was replaced with 3 mL/well of assay medium [Leibovitz's L-15 medium plus 0.6% glucose, 1% FCS, 1% N-2 supplement (Gibco), 10 μM ara-C, 10 mM Hepes, and penicillin/streptomycin/glutamine] containing either vehicle (DMSO, 1/200,000), positive control (2–4 ng/mL NGF) or test compound (50–250 nM). All media were prepared fresh daily. DRG were microscopically examined for neurite outgrowth on days 1–5. Under optimal conditions, vehicle treatment did not induce neurite outgrowth from DRG. An experiment was considered positive (+) if the instant compound induced neurites of ≧1 diameter of the DRG.

EXAMPLE 8

Primary Rat Hippocampal Cells

Hippocampal cells were dissected from the brains of embryonic day 18 rat pups and dissociated with trypsin (1 mg/mL) and trituration. Cells were seeded at 30,000 cells/well in 96-well plates filled with 100 μL MEM and 10% FBS. At 7 days in culture, cells were fixed with 4% paraformaldehyde and immuno-fluorescence is performed.

EXAMPLE 9

Human M17 Neuroblastoma Cells

M17 human neuroblastoma cells were cultured in 1:1 ratio of EMEM and Ham's F12 with 1×NEAA and 10% FBS. The culture media contained 1×PSN antibiotic and was exchanged every other day, and the cells were passed in log phase near confluence.

TABLE 1

| Cmpd | | MS (M + 1) + | DRG | Rat Hippocampal Cell Response | M17 Cell Response |
|---|---|---|---|---|---|
| (1) | | 238 | + | 123 | 115 |
| (2) | | 356 | NT | <100 | <100 |

In Vitro Neurotrophic Activity

TABLE 1-continued

In Vitro Neurotrophic Activity

| Cmpd | MS (M + 1) + | DRG | Rat Hippocampal Cell Response | M17 Cell Response |
|---|---|---|---|---|
| (3) | 357 | NT | 145 | <100 |
| (4) | 252 | NT | 140 | <100 |
| (5) | 268 | NT | 105 | <100 |
| (6) | 462 | NT | 105 | <100 |

+=Positive results for each experiment
NT=Not tested

EXAMPLE 10

Neurite Outgrowth Assay

Cultures were incubated with normal horse serum (1:50; Vector Labs) or about 20 min, rinsed and then incubated with primary antibody, microtubule associated-protein 2 (anti-mouse MAP-2; 1:1000; Chemicon) for about 2 h at about RT. Following primary antibody, cultures were rinsed and incubated with fluorescein anti-mouse IgG (rat absorbed; 1:50; Vector Labs) for about 1 h. After fluorescein incubation, the cultures were rinsed and read in PBS on a fluorescent plate reader (excitation: 485 nm; emission: 530 nm). A compound was regarded as active if the neurite outgrowth response is greater than the mean DMSO-treated control response on the same plate. The response to test compound was reported as percent of DMSO-treated control. The signal-to-noise separation is consistent: the fluorescence from DMSO control wells is at least twofold greater than blank wells.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula I or II,

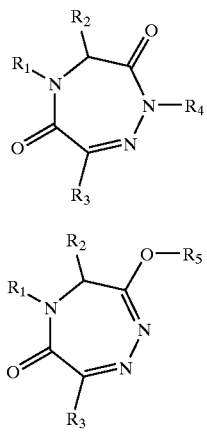

or a pharmaceutically acceptable salt thereof, wherein
$R_1$, $R_2$, $R_3$, and $R_4$ are independently selected from hydrogen, $C_1$–$C_{10}$ alkyl, aryl, and heterocyclyl, or $R_1$, the nitrogen atom attached to $R_1$, and $R_2$ together form a 4- to 8-membered heterocycle having 1 to 4 heteroatoms selected from the group consisting of S, O, and N; and
$R_5$ is selected from $C_1$–$C_{10}$ alkyl, aryl, and heterocyclyl, or $R_1$, the nitrogen atom attached to $R_1$, and $R_2$ together form a 4- to 8-membered heterocycle having 1 to 4 heteroatoms selected from the group consisting of S, O, and N.

2. The compound of claim 1 having the structure of Formula Ia or IIa,

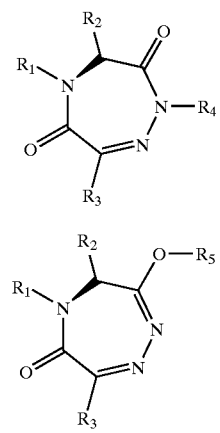

wherein $R_1$, $R_2$, $R_3$, $R_4$, and $R_5$ are as claimed in claim 1.

3. The compound of claim 2, wherein $R_4$ is hydrogen or $C_1$–$C_{10}$ alkyl substituted with aryl or N-containing heterocyclyl.

4. The compound of claim 2, wherein $R_3$ is $C_4$–$C_{10}$ alkyl.

5. The compound of claim 2, wherein $R_1$, the nitrogen atom attached to $R_1$, and $R_2$ together form a 4- to 8-membered heterocycle having 1 to 4 heteroatoms selected from the group consisting of S, O, and N.

6. The compound of claim 5, wherein $R_1$, the nitrogen atom attached to $R_1$, and $R_2$ together form

7. The compound of claim 1 which is 1H-pyrrolo[2,1-d][1,2,5]triazepine-1,5(2H)-dione, 4-(1,1-dimethylpropyl)-7,8,9,9a-tetrahydro-.

8. The compound of claim 1 which is 1H-pyrrolo[2,1-d][1,2,5]triazepine-1,5(2H)-dione, 4-(1,1-dimethylpropyl)-7,8,9,9a-tetrahydro-2-[3-(3-pyridinyl)propyl]-, (9aS)-.

9. A pharmaceutical composition comprising the compound of claim 1 and a pharmaceutically acceptable carrier.

10. A process for preparing the compound of Formula Ia wherein $R_{3a}$ is selected from $C_1$–$C_{10}$ alkyl, aryl, and heterocyclyl, or $R_1$, the nitrogen atom $R_1$ is attached to, and $R_2$ together form a 4- to 8-membered heterocycle having 1 to 4 heteroatoms selected from the group consisting of S, O, and N,

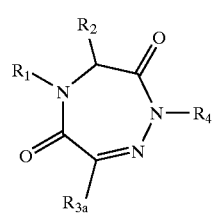

which process comprises:

(a) reacting compound 1 with compound 2 to form compound 3;

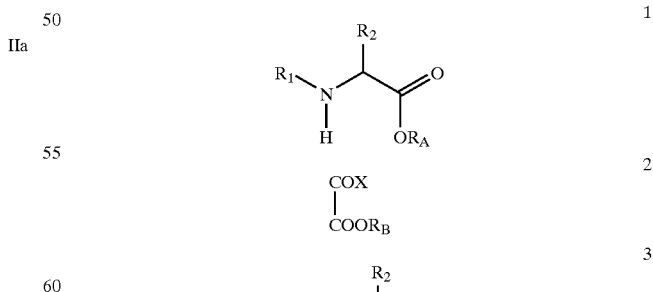

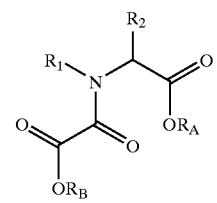

-continued

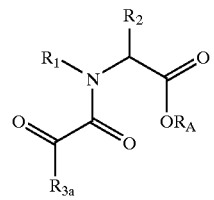
4

(b) reacting compound 3 with $R_{3a}$-M to form compound 4; and (c) reacting compound 4 with $H_2N-NHR_4$ to form the compound Ia.

11. A process for preparing the compound of Formula Id and II,

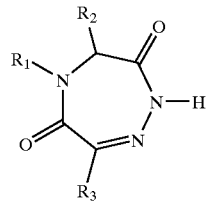
Ic

-continued

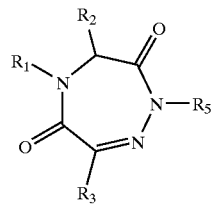
Id

II which process comprises reacting compound Ic with $R_5Y$, wherein Y is halogen, to form compounds Id and II.

12. A process of claim 11, further comprising the step of separating compounds Ic and II by chromatography.

* * * * *